US012799124B2

(12) United States Patent
Kim et al.

(10) Patent No.: US 12,799,124 B2
(45) Date of Patent: Nov. 17, 2026

(54) PROCESS FOR PREPARING 5-(4-(2,6-DIFLUORO-4-(2-METHOXYETHOXY)PHENYL)PIPERAZIN-1-YL)-3-METHYL-3,6-DIHYDRO-7H-[1,2,3]TRIAZOLO[4,5-D]PYRIMIDIN-7-ONE

(71) Applicant: ST PHARM CO., LTD., Gyeonggi-do (KR)

(72) Inventors: Kyung Jin Kim, Seoul (KR); Uk-Il Kim, Gyeonggi-do (KR); Hyuang Tae Bang, Gyeonggi-do (KR); Seul Ki Lee, Gyeonggi-do (KR); Si Yeon Han, Gyeonggi-do (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 274 days.

(21) Appl. No.: 18/714,275

(22) PCT Filed: Dec. 1, 2021

(86) PCT No.: PCT/KR2021/018043
§ 371 (c)(1),
(2) Date: May 29, 2024

(87) PCT Pub. No.: WO2023/101048
PCT Pub. Date: Jun. 8, 2023

(65) Prior Publication Data

US 2025/0034152 A1 Jan. 30, 2025

(51) Int. Cl.
*C07D 241/04* (2006.01)
*C07D 487/04* (2006.01)

(52) U.S. Cl.
CPC .................................. *C07D 487/04* (2013.01)

(58) Field of Classification Search
CPC .................................................... C07D 241/04
USPC .......................................................... 544/386
See application file for complete search history.

(56) References Cited

U.S. PATENT DOCUMENTS

2017/0145016 A1 5/2017 Heo et al.
2018/0051030 A1 2/2018 Lim et al.

FOREIGN PATENT DOCUMENTS

| | | | |
|---|---|---|---|
| CN | 1020150005711 | | 1/2015 |
| CN | 1020150016406 | | 2/2015 |
| JP | 2005-502683 | A | 1/2005 |
| KR | 10-2015-0005711 | | 1/2015 |
| KR | 10-2015-0016406 | | 2/2015 |
| WO | WO 2016/006974 | A2 | 1/2016 |

OTHER PUBLICATIONS

Supplementary European Search Report issued for European Application No. EP 21966474, dated Jan. 3, 2025, 8 pages.
Angiolini et al., "Solid-phase synthesis of pyrido[2,3-d]pyrimidin-7-ones," *Tetrahedron Letters*, 46; pp. 8749-8752, 2005.
International Search Report and Written Opinion (with English-language translation) for International Application No. PCT/KR2021/018043, mailed Aug. 22, 2022, 4 pages.
Notice of Reasons for Refusal issued for Japanese Patent Application No. 2024-531076, dated May 19, 2025, 9 pages, with English Translation.

*Primary Examiner* — Douglas M Willis
(74) *Attorney, Agent, or Firm* — Klarquist Sparkman, LLP

(57) ABSTRACT

The present disclosure concerns a method for preparing a triazolopyrimidinone derivative exhibiting tankyrase inhibitory activity and an intermediate thereof. The disclosed method comprises preparing triazolopyrimidine and fluorinated arylpiperazine intermediates, coupling these intermediates to form a protected triazolopyrimidinone precursor, and deprotecting the protected triazolopyrimidinone precursor. In certain embodiments, the triazolopyrimidine intermediate is prepared by protecting and oxidizing a triazolopyrimidinone starting material. In certain embodiments, the fluorinated arylpiperazine intermediate is prepared using a fluorinated benzaldehyde starting material and a sequence comprising amination, a Dakin reaction, and alkylation. In some embodiments, the fluorinated arylpiperazine and triazolopyrimidine intermediates are coupled prior to performing the Dakin reaction and alkylation of the fluorinated arylpiperazine intermediate. The methods provide shortened synthetic routes that permit isolation of intermediates and products at high purity and yield, thereby facilitating economical and scalable manufacture of the triazolopyrimidinone derivative.

10 Claims, No Drawings

PROCESS FOR PREPARING 5-(4-(2,6-DIFLUORO-4-(2-METHOXYETHOXY)PHENYL)PIPERAZIN-1-YL)-3-METHYL-3,6-DIHYDRO-7H-[1,2,3]TRIAZOLO[4,5-D]PYRIMIDIN-7-ONE

TECHNICAL FIELD

The present invention relates to a method for preparing a triazolopyrimidinone derivative exhibiting tankyrase inhibitory activity.

BACKGROUND ART

Tankyrase belongs to the poly(ADP-ribose) polymerase (PARP) protein family, which consists of 17 members that share a catalytic PARP domain. It has been recently reported that intracellular axin levels are influenced by the PARP enzyme family members tanykyrase-1 and tanykyrase-2 (also known as PARP5a and PARP5b, respectively) (Huang et al., 2009, Nature, 461(7264): 614-620).

Inhibitors of tankyrase-1 and tankyrase-2 are known to be effective in a variety of cancer diseases, such as solid cancers including colorectal carcinoma, colon cancer, gastric cancer, hepatocellular carcinoma, breast cancer, medulloblastoma, melanoma, non-small cell lung cancer, pancreas adenocarcinoma, and prostate cancer. In addition, the inhibitors of tankyrase-1 and tankyrase-2 have therapeutic potential for diseases other than cancer, including osteoporosis, osteoarthritis, polycystic kidney disease, pulmonary fibrosis, diabetes, schizophrenia, vascular disease, cardiac disease, non-oncogenic proliferative disease, and neurodegenerative diseases such as Alzheimer's disease.

As noted above, there is an ongoing need for novel therapeutics for cancer and overgrowth conditions, and the development of novel pharmaceutical compounds capable of selectively inhibiting the enzyme tankyrase has been attempted. In particular, a triazolopyrimidinone derivative represented by the following Chemical Formula I is known as a selective tankyrase inhibitor and is being developed for the treatment of colorectal cancer in patients with Kirsten rat sarcoma viral oncogene homolog (KRAS) mutant genotypes or in patients with no response to Erbitux:

[Chemical Formula I]

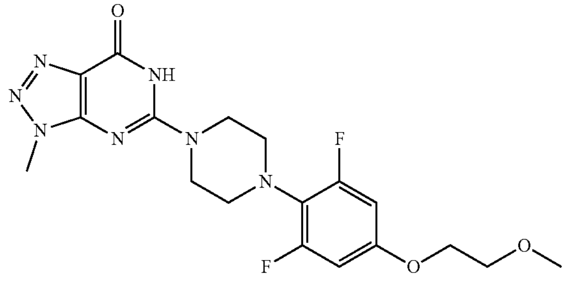

International Publication WO 2016/006974 discloses a method for preparing a triazolopyrimidinone derivative, including the compound of Chemical Formula I above. However, the above preparation method includes a reaction process using microwaves and column purification, and is not suitable for mass production, which requires process improvement.

Therefore, there is a need to develop a novel method capable of preparing the triazolopyrimidinone derivative compound of Chemical Formula I with high purity while improving the above inefficient preparation method.

DISCLOSURE

Technical Problem

An object of the present invention is to provide a method for preparing a triazolopyrimidinone derivative with high purity and high yield, thereby lowering the production cost and performing efficient process steps to be suitable for mass production.

Another object of the present invention is to provide a novel intermediate used in the above preparation method.

Technical Solution

The present invention provides a method for preparing a triazolopyrimidinone derivative represented by the following Chemical Formula I:

[Chemical Formula I]

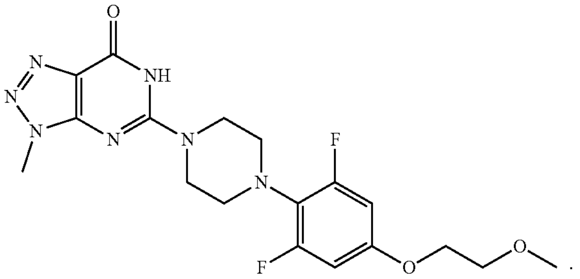

According to an embodiment of the present invention, the triazolopyrimidinone derivative represented by Chemical Formula I above may be prepared via the synthetic routes A or B below.

Synthesis Route A

Synthesis route A of the preparation method of the present invention comprises Steps (A-1) to (A-8) below:

(A-1) Step 1 of preparing a compound represented by the following Chemical Formula 2 by a protection reaction from a compound represented by the following Chemical Formula 1 or a salt thereof;

(A-2) Step 2 of preparing a compound represented by the following Chemical Formula 3 by an oxidation reaction from the compound represented by Chemical Formula 2;

(A-3) Step 3 of preparing a compound represented by the following Chemical Formula 5 by an amination reaction from a compound represented by the following Chemical Formula 4;

(A-4) Step 4 of preparing a compound represented by the following Chemical Formula 6 by a Dakin reaction from the compound represented by Chemical Formula 5;

(A-5) Step 5 of preparing a compound represented by the following Chemical Formula 7 by an alkylation reaction from the compound represented by Chemical Formula 6;

(A-6) Step 6 of preparing a compound represented by the following Chemical Formula 8 or a salt thereof by a deprotection reaction from the compound represented by Chemical Formula 7;

(8) Step 7 of preparing a compound represented by the following Chemical Formula Ia by an amination reaction from the compound represented by Chemical Formula 3 and the compound represented by Chemical Formula 8 or a salt thereof; and (A-8) Step 8 of preparing a compound represented by the following Chemical Formula I by a deprotection reaction from the compound represented by Chemical Formula Ia;

[Chemical Formula 1]

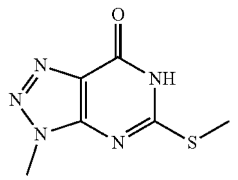

[Chemical Formula 2]

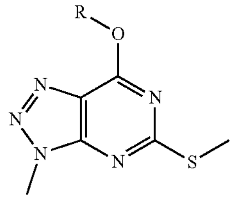

[Chemical Formula 3]

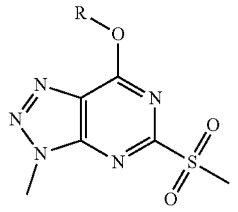

[Chemical Formula 4]

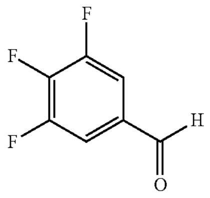

[Chemical Formula 5]

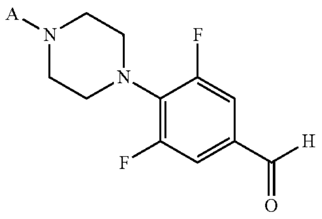

[Chemical Formula 6]

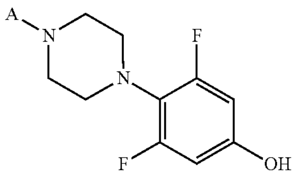

-continued

[Chemical Formula 7]

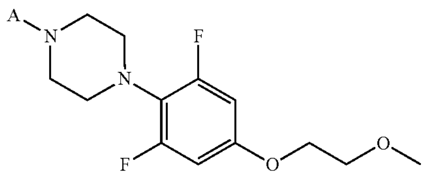

[Chemical Formula 8]

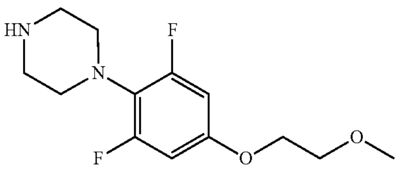

[Chemical Formula Ia]

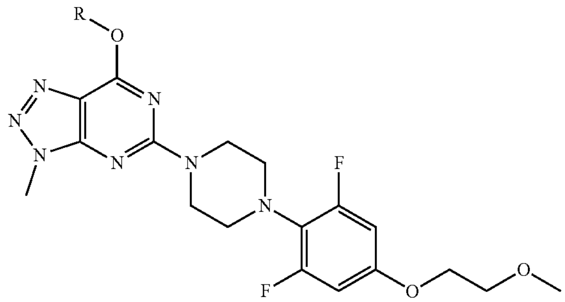

[Chemical Formula I]

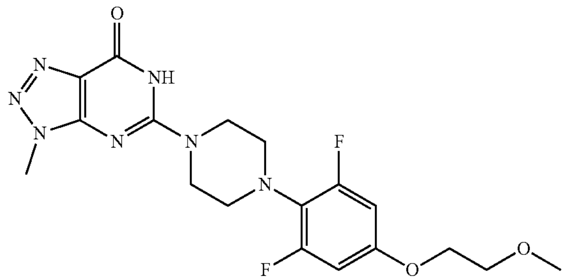

in the Chemical Formulas,

R is an O-protecting group; and

A is an N-protecting group.

Hereinafter, Steps (A-1) to (A-8) will be described separately.

Step (A-1)

In the present invention, Step (A-1) is a step of preparing the compound represented by Chemical Formula 2 through a protection reaction using the triazolopyrimidinone derivative compound represented by Chemical Formula 1 or a salt thereof as a starting material (Reaction Scheme 1):

[Reaction Scheme 1]

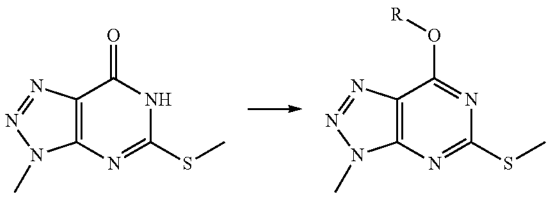

in the Chemical Formula, R is an O-protecting group.

According to an embodiment of the present invention, the above reaction proceeds to the protection of the triazolopyrimidinone derivative. For example, R may be $C_1$-$C_6$ alkyl, acetyl, benzoyl, benzyl, p-methoxybenzyl, methoxymethyl acetal (MOM), tetrahydropyran (THP), or silyl ether. According to an embodiment of the present invention, in the above reaction, the compound represented by Chemical Formula 1 may be reacted with an alkyl halide to prepare the compound represented by Chemical Formula 2. For example, R may be isopropyl and the reaction may be performed by an alkylation reaction with 2-iodopropane, but is not limited thereto.

In the reaction, any base conventionally used in protection reactions may be used. For example, the base may be sodium hydroxide, potassium hydroxide, potassium carbonate, sodium carbonate, sodium bicarbonate, cesium carbonate, or cesium fluoride. Specifically, cesium fluoride (CsF) may be used, but the base is not limited thereto.

In the reaction, any organic solvent conventionally used in protection reactions may be used. For example, the solvent may be acetonitrile, tetrahydrofuran, 1,4-dioxane, acetone, dimethyl sulfoxide, dimethyl acetamide, dimethyl formamide, or a mixture thereof. Specifically, dimethylformamide may be used, but the solvent is not limited thereto.

Further, the reaction may be performed at 30 to 110° C., and more specifically, may be performed at 60 to 90° C., but is not limited thereto.

The method may further comprise, after the above reaction, one or more steps of separating or purifying the resulting product, but is not limited thereto. In this Example of the present invention, the product of the above reaction was stirred in an organic solvent, isopropanol, to afford the desired product with high purity.

Step (A-2)

In the present invention, Step (A-2) is a step of preparing the compound represented by Chemical Formula 3 through an oxidation reaction using the triazolopyrimidinone derivative compound represented by Chemical Formula 2 as a starting material (Reaction Scheme 2):

[Reaction Scheme 2]

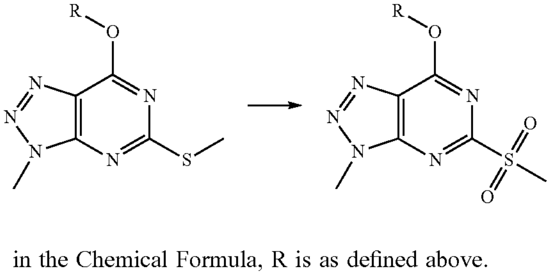

in the Chemical Formula, R is as defined above.

According to an embodiment of the present invention, the reaction may be performed by an oxidation reaction in which the compound represented by Chemical Formula 2 is reacted with an oxidizing agent.

In the reaction, any oxidizing agent conventionally used in oxidation reactions may be used. For example, hydrogen peroxide, benzoyl peroxide, meta-chloroperoxybenzoic acid, or oxone may be used as the oxidizing agent. Specifically, oxone may be used, but the oxidizing agent is not limited thereto.

In the reaction, any organic solvent conventionally used in oxidation reactions may be used. For example, the solvent may be tetrahydrofuran, 1,4-dioxane, acetone, methanol, ethanol, isopropanol, water or a mixture thereof. Specifically, a mixture of tetrahydrofuran and methanol may be used, but the solvent is not limited thereto.

Further, the reaction may be performed at 0 to 70° C., and more specifically, may be performed at 30 to 50° C., but is not limited thereto.

The method may further comprise, after the above reaction, one or more steps of separating or purifying the resulting product, but is not limited thereto. In this Example of the present invention, the product of the above reaction was stirred in an organic solvent, isopropanol, to afford the desired product with high purity.

Step (A-3)

In the present invention, Step (A-3) is a step of preparing the compound represented by Chemical Formula 5 through an amination reaction using the trifluorobenzaldehyde derivative compound represented by Chemical Formula 4 as a starting material (Reaction Scheme 3):

[Reaction Scheme 3]

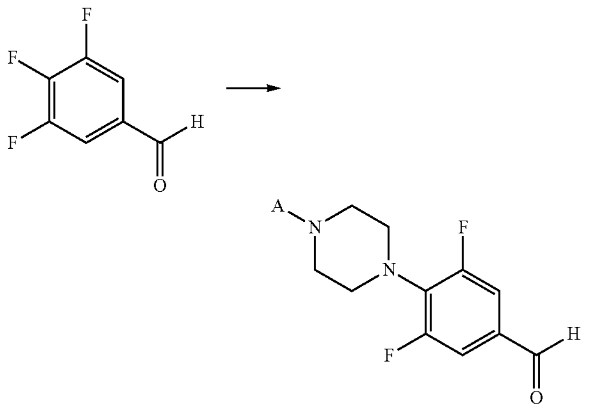

in the Chemical Formula, A is an N-protecting group.

According to an embodiment of the present invention, in the reaction, trifluorobenzaldehyde derivatives and protected piperazine derivatives may be used. For example, A may be -Boc, -Cbz, -Fmoc, -benzyl, p-methoxybenzyl, trityl or dimethoxytrityl (DMT). According to an embodiment of the present invention, the reaction may be performed by an amination reaction in which 3,4,5-trifluorobenzaldehyde is reacted with N-Boc-piperazine, but is not limited thereto.

In the reaction, any base conventionally used in amination reactions may be used. For example, the base may be lithium carbonate, sodium carbonate, potassium carbonate, sodium bicarbonate, or cesium carbonate. Specifically, lithium carbonate may be used, but the base is not limited thereto.

In the reaction, any organic solvent conventionally used in amination reactions may be used. For example, the solvent may be acetonitrile, tetrahydrofuran, 1,4-dioxane, acetone, dimethyl sulfoxide, dimethyl acetamide, dimethyl formamide, or a mixture thereof. Specifically, dimethyl sulfoxide may be used, but the solvent is not limited thereto.

Further, the reaction may be performed at 80 to 150° C., and more specifically, may be performed at 110 to 130° C., but is not limited thereto.

The method may further comprise, after the above reaction, one or more steps of separating or purifying the resulting product, but is not limited thereto.

Step (A-4)

In the present invention, Step (A-4) is a step of preparing the compound represented by Chemical Formula 6 through a Dakin reaction using the phenylpiperazine derivative compound represented by Chemical Formula 5 as a starting material (Reaction Scheme 4):

[Reaction Scheme 4]

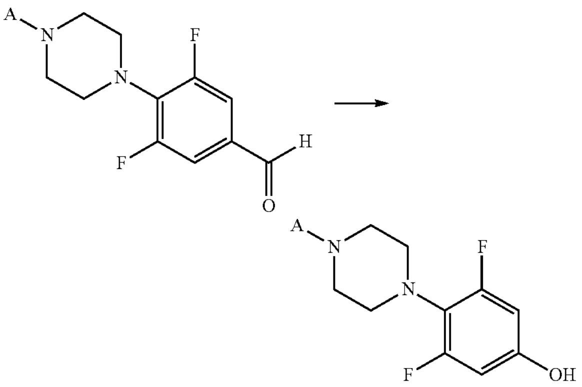

in the Chemical Formula, A is as defined above.

According to an embodiment of the present invention, the reaction may be performed by adding an oxidizing agent to the compound represented by Chemical Formula 5.

In the Dakin reaction, a commonly used oxidizing agent may be used. For example, hydrogen peroxide, ammonium persulfate, meta-chloroperoxybenzoic acid (mCPBA), or a mixture thereof may be used. Specifically, meta-chloroperoxybenzoic acid may be used, but the oxidizing agent is not limited thereto.

It is possible to use a commonly used base when hydrolyzing the intermediate (phenyl formate) obtained after the above reaction. For example, the base may be lithium hydroxide, sodium hydroxide, potassium hydroxide, sodium bicarbonate, sodium carbonate, or calcium carbonate. Specifically, sodium hydroxide may be used, but the base is not limited thereto.

In the above reaction, a commonly used solvent may be used. For example, the solvent may be dichloromethane, chloroform, tetrahydrofuran, 1,4-dioxane, acetone, methanol, ethanol, isopropanol, water, or a mixture thereof. Specifically, dichloromethane may be used, but the solvent is not limited thereto.

Further, the reaction may be performed at −20 to 30° C., and more specifically, may be performed at −15 to 15° C., but is not limited thereto.

The method may further comprise, after the above reaction, one or more steps of separating or purifying the resulting product, but is not limited thereto. For example, in this Example of the present invention, the product of the above reaction was stirred in an organic solvent, isopropanol, to afford the desired product with high purity.

Step (A-5)

In the present invention, Step (A-5) is a step of preparing the compound represented by Chemical Formula 7 through an alkylation reaction using the phenylpiperazine derivative compound represented by Chemical Formula 6 as a starting material (Reaction Scheme 5):

[Reaction Scheme 5]

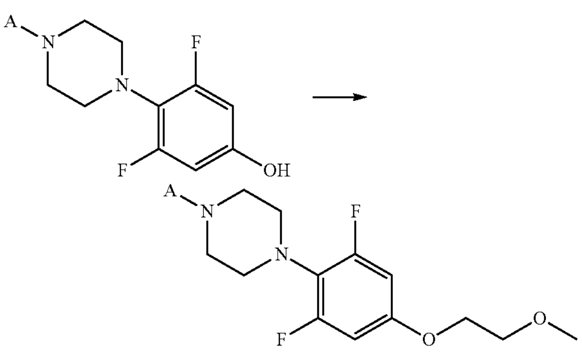

in the Chemical Formula, A is as defined above.

According to an embodiment of the present invention, the reaction may be performed by an alkylation reaction in which the compound represented by Chemical Formula 6 is reacted with 1-halo-2-methoxyethane (for example, 1-bromo-2-methoxyethane).

In the reaction, any organic solvent conventionally used in alkylation reactions may be used. For example, the solvent may be acetonitrile, tetrahydrofuran, 1,4-dioxane, acetone, dimethyl sulfoxide, dimethyl acetamide, dimethyl formamide, or a mixture thereof. Specifically, acetonitrile may be used, but the solvent is not limited thereto.

Further, the reaction may be performed at 50 to 100° C., and more specifically, may be performed at 75 to 85° C., but is not limited thereto.

Step (A-6)

In the present invention, Step (A-6) is a step of preparing the compound represented by Chemical Formula 8 or a salt thereof through a deprotection reaction using the phenylpiperazine derivative compound represented by Chemical Formula 7 as a starting material (Reaction Scheme 6):

[Reaction Scheme 6]

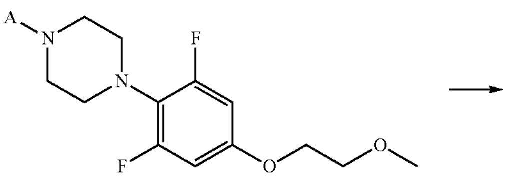

-continued

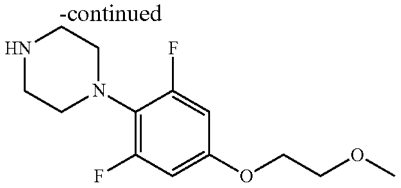

in the Chemical Formula, A is as defined above.

According to an embodiment of the present invention, the reaction may be performed by a deprotection reaction of the compound represented by Chemical Formula 7 under acidic conditions.

In the reaction, any solvent conventionally used in deprotection reactions may be used. For example, the solvent may be methanol, ethanol, isopropanol, tetrahydrofuran, acetonitrile, water, or a mixture thereof. Specifically, methanol may be used, but the solvent is not limited thereto.

Further, the reaction may be performed at 0 to 60° C., and more specifically, may be performed at 30 to 50° C., but is not limited thereto.

The method may further comprise, after the above reaction, one or more steps of separating or purifying the resulting product, but is not limited thereto. In this Example of the present invention, the product of the above reaction was stirred in an organic solvent, dichloromethane, tert-butyl methyl ether, or a mixture thereof, to afford the desired product with high purity.

Step (A-7)

In the present invention, Step (A-7) is a step of preparing the compound represented by Chemical Formula Ia by an amination reaction from the compound represented by Chemical Formula 3 and the compound represented by Chemical Formula 8 or a salt thereof (Reaction Scheme 7):

[Reaction Scheme 7]

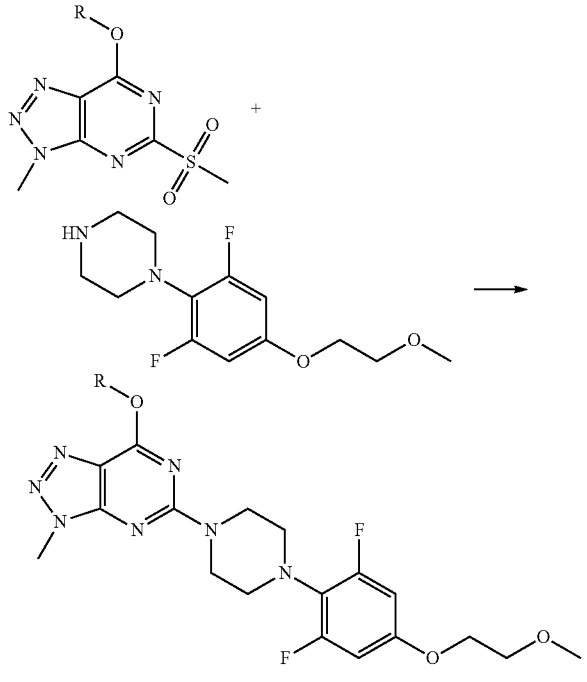

in the Chemical Formula, R is as defined above.

According to an embodiment of the present invention, the reaction may be performed by an amination reaction using, for example, 7-isopropoxy-3-methyl-5-(methylsulfonyl)-3H-[1,2,3]triazolo[4,5-d]pyrimidine and 1-(2,6-difluoro-4-(2-methoxyethoxy)phenyl)piperazine hydrochloride.

In the reaction, any base conventionally used in amination reactions may be used. For example, the base may be lithium carbonate, sodium carbonate, potassium carbonate, sodium bicarbonate, cesium carbonate, triethylamine, diisopropylethylamine, or 1,8-diazabicyclo[5,4,0]undec-7-ene (DBU). Specifically, diisopropylethylamine may be used, but the base is not limited thereto.

In the reaction, any organic solvent conventionally used in amination reactions may be used. For example, the solvent may be acetonitrile, tetrahydrofuran, 1,4-dioxane, acetone, dimethyl sulfoxide, dimethyl acetamide, dimethyl formamide, methanol, ethanol, isopropanol, or a mixture thereof. Specifically, ethanol may be used, but the solvent is not limited thereto.

Further, the reaction may be performed at 50 to 100° C., and more specifically, may be performed at 60 to 80° C., but is not limited thereto.

The method may further comprise, after the above reaction, one or more steps of separating or purifying the resulting product, but is not limited thereto. In this Example of the present invention, the product of the above reaction was stirred in an organic solvent, dichloromethane, diisopropyl ether, or a mixture thereof, to afford the desired product with high purity.

Step (A-8)

In the present invention, Step (A-8) is a step of preparing the compound represented by Chemical Formula I by a deprotection reaction from the compound represented by Chemical Formula Ia (Reaction Scheme 8):

[Reaction Scheme 8]

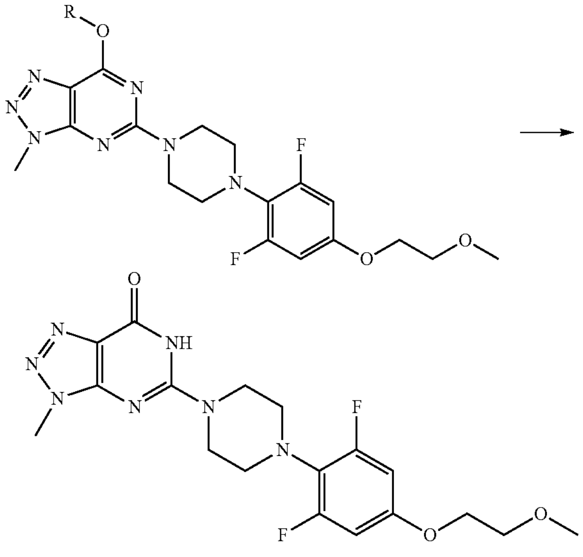

in the Chemical Formula, R is as defined above.

According to an embodiment of the present invention, the reaction may be, for example, performed by a deprotection reaction from 5-(4-(2,6-difluoro-4-(2-methoxyethoxy)phenyl)piperazin-1-yl)-7-isopropoxy-3-methyl-3H-[1,2,3]triazolo[4,5-d]pyrimidine.

In the above reaction, any acid conventionally used in deprotection reactions may be used as the solvent. At this time, the acid may be acetic acid, hydrochloric acid, sulfuric acid, nitric acid, phosphoric acid, or a mixture thereof. Specifically, acetic acid, sulfuric acid, or a mixture thereof may be used, but the acid is not limited thereto.

Further, the reaction may be performed at 30 to 80° C., and more specifically, may be performed at 40 to 60° C., but is not limited thereto.

The method may further comprise, after the above reaction, one or more steps of separating or purifying the resulting product, but is not limited thereto. In this Example of the present invention, the product of the above reaction was stirred in acetone, water or a mixture thereof, to afford the desired product with high purity.

Synthesis Route B

Synthesis route B of the preparation method of the present invention comprises Steps (B-1) to (B-7) below:

(B-1) Step 1 of preparing a compound represented by the following Chemical Formula 2 by a protection reaction from a compound represented by the following Chemical Formula 1 or a salt thereof;

(B-2) Step 2 of preparing a compound represented by the following Chemical Formula 3 by an oxidation reaction from the compound represented by Chemical Formula 2;

(B-3) Step 3 of preparing a compound represented by the following Chemical Formula 9 by an amination reaction from a compound represented by the following Chemical Formula 4;

(B-4) Step 4 of preparing a compound represented by the following Chemical Formula 10 by an amination reaction from the compound represented by Chemical Formula 3 and the compound represented by Chemical Formula 9 or a salt thereof;

(B-5) Step 5 of preparing a compound represented by the following Chemical Formula 11 by a Dakin reaction from the compound represented by Chemical Formula 10;

(B-6) Step 6 of preparing a compound represented by the following Chemical Formula Ia by an alkylation reaction from the compound represented by Chemical Formula 11; and (B-7) Step 7 of preparing a compound represented by the following Chemical Formula I by a deprotection reaction from the compound represented by Chemical Formula Ia:

[Chemical Formula 1]

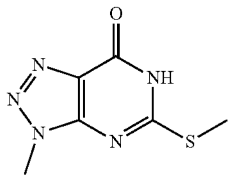

-continued

[Chemical Formula 2]

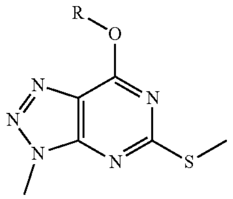

[Chemical Formula 3]

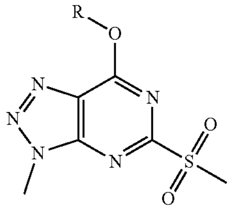

[Chemical Formula 4]

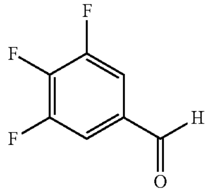

[Chemical Formula 9]

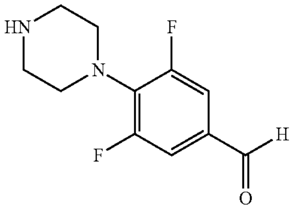

[Chemical Formula 10]

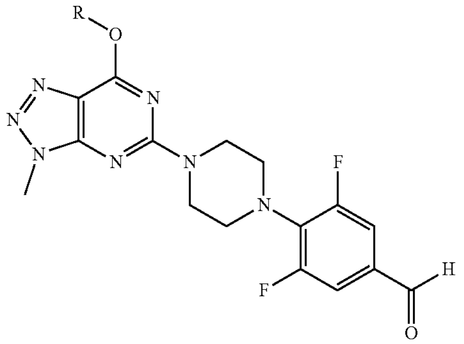

[Chemical Formula 11]

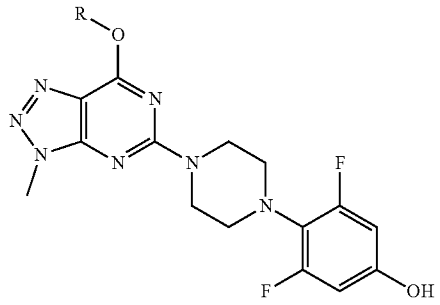

-continued

[Chemical Formula Ia]

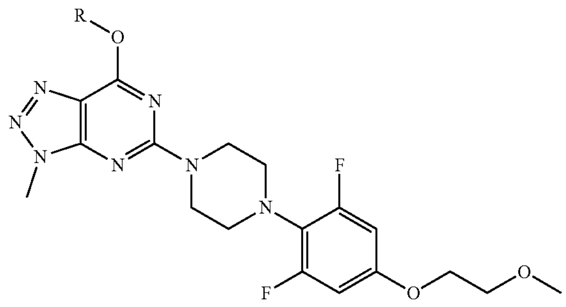

[Chemical Formula I]

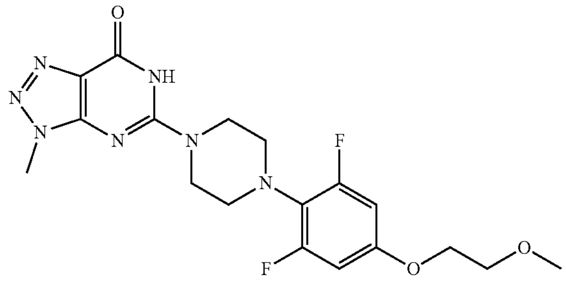

in the Chemical Formulas,

R is an O-protecting group.

Hereinafter, Steps (B-1) to (B-7) will be described separately. Among these, Steps (B-1), (B-2), and (B-7) are the same as Steps (A-1), (A-2), and (A-8) described above, respectively, and thus Steps (B-3) through (B-6) will be merely discussed in detail.

Step (B-3)

In the present invention, Step (B-3) is a step of preparing the compound represented by Chemical Formula 9 or a salt thereof through an amination reaction using the trifluorobenzaldehyde derivative compound represented by Chemical Formula 4 as a starting material (Reaction Scheme 9):

[Reaction Scheme 9]

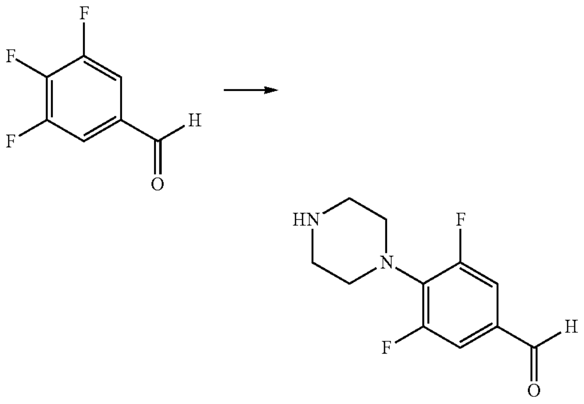

According to an embodiment of the present invention, in the reaction, trifluorobenzaldehyde derivatives and piperazine may be used.

In the reaction, any base conventionally used in amination reactions may be used. For example, the base may be lithium carbonate, sodium carbonate, potassium carbonate, sodium bicarbonate, or cesium carbonate. Specifically, potassium carbonate may be used, but the base is not limited thereto.

In the reaction, any organic solvent conventionally used in amination reactions may be used. For example, the solvent may be acetonitrile, tetrahydrofuran, 1,4-dioxane, acetone, isopropyl alcohol, dimethyl sulfoxide, dimethylacetamide, dimethylformamide, ethylene glycol, diethylene glycol, dimethyl ether, dimethoxyethane, or a mixture thereof. Specifically, dimethoxyethane may be used, but the solvent is not limited thereto.

Further, the reaction may be performed at 60 to 150° C., and more specifically, may be performed at 70 to 90° C., but is not limited thereto.

The method may further comprise, after the above reaction, one or more steps of separating or purifying the resulting product, but is not limited thereto.

Step (B-4)

In the present invention, Step (B-4) is a step of preparing the compound represented by Chemical Formula 10 by an amination reaction from the compound represented by Chemical Formula 3 and the compound represented by Chemical Formula 9 or a salt thereof (Reaction Scheme 10):

[Reaction Scheme 10]

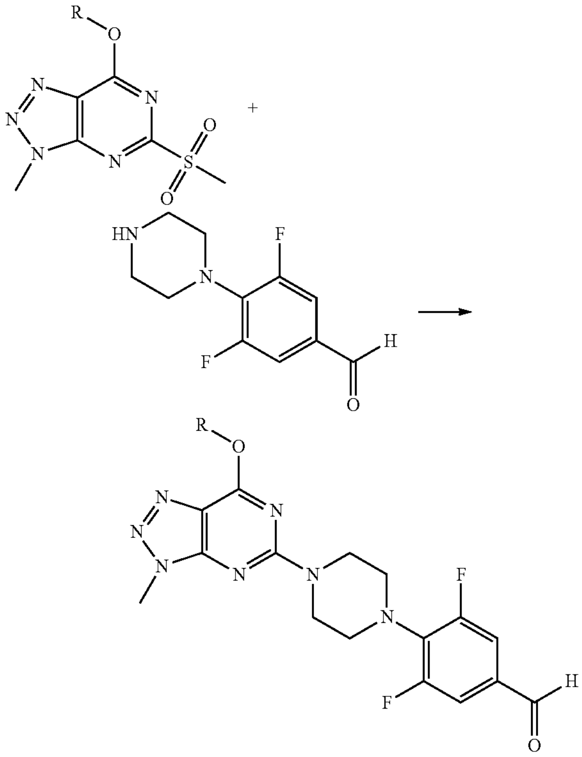

in the Chemical Formula, R is as defined above.

According to an embodiment of the present invention, the reaction may be performed by an amination reaction using, for example, 7-isopropoxy-3-methyl-5-(methylsulfonyl)-3H-[1,2,3]triazolo[4,5-d]pyrimidine and 3,5-difluoro-4-(piperazin-1-yl)benzaldehyde.

In the reaction, any base conventionally used in amination reactions may be used. For example, the base may be lithium carbonate, sodium carbonate, potassium carbonate, sodium bicarbonate, cesium carbonate, triethylamine, diisopropylethylamine, or 1,8-diazabicyclo[5,4,0]undec-7-ene (DBU), but is not limited thereto.

In the reaction, any organic solvent conventionally used in amination reactions may be used. For example, the solvent may be acetonitrile, tetrahydrofuran, 1,4-dioxane, acetone, dimethyl sulfoxide, dimethyl acetamide, dimethyl formamide, methanol, ethanol, isopropanol, or a mixture thereof. Specifically, dimethyl acetamide may be used, but the solvent is not limited thereto.

Further, the reaction may be performed at 50 to 150° C., and more specifically, may be performed at 80 to 120° C., but is not limited thereto.

The method may further comprise, after the above reaction, one or more steps of separating or purifying the resulting product, but is not limited thereto. In this Example of the present invention, the product of the above reaction was stirred in an organic solvent, diethyl ether, isopropanol, or a mixture thereof, to afford the desired product with high purity.

Step (B-5)

In the present invention, Step (B-5) is a step of preparing the compound represented by Chemical Formula 11 through a Dakin reaction using the compound represented by Chemical Formula 10 as a starting material (Reaction Scheme 11):

[Reaction Scheme 11]

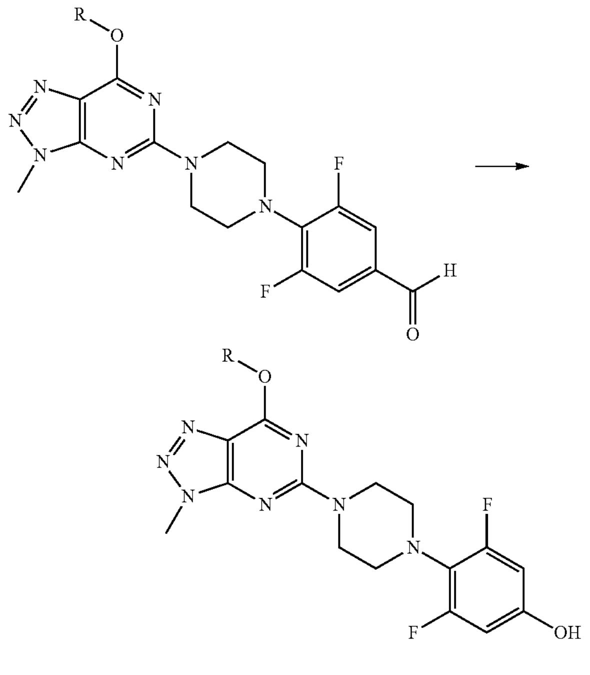

in the Chemical Formula, R is as defined above.

According to an embodiment of the present invention, the reaction may be performed by adding an oxidizing agent to the compound represented by Chemical Formula 10.

In the Dakin reaction, a commonly used oxidizing agent may be used. For example, hydrogen peroxide, ammonium persulfate, meta-chloroperoxybenzoic acid (mCPBA), or a mixture thereof may be used. Specifically, meta-chloroperoxybenzoic acid may be used, but the oxidizing agent is not limited thereto.

It is possible to use a commonly used base when hydrolyzing the intermediate (phenyl formate) obtained after the above reaction. For example, the base may be lithium hydroxide, sodium hydroxide, potassium hydroxide, sodium bicarbonate, sodium carbonate, or calcium carbonate. Specifically, sodium hydroxide may be used, but the base is not limited thereto.

In the above reaction, a commonly used solvent may be used. For example, the solvent may be dichloromethane, chloroform, tetrahydrofuran, 1,4-dioxane, acetone, methanol, ethanol, isopropanol, water, or a mixture thereof. Specifically, dichloromethane may be used, but the solvent is not limited thereto.

Further, the reaction may be performed at −20 to 30° C., and more specifically, may be performed at −15 to 15° C., but is not limited thereto.

The method may further comprise, after the above reaction, one or more steps of separating or purifying the resulting product, but is not limited thereto. In this Example of the present invention, the product of the above reaction was stirred in an organic solvent, isopropanol, tert-butyl methyl ether, or a mixture thereof, to afford the desired product with high purity.

Step (B-6)

In the present invention, Step (B-6) is a step of preparing the compound represented by Chemical Formula Ia through an alkylation reaction using the compound represented by Chemical Formula 11 as a starting material (Reaction Scheme 12):

[Reaction Scheme 12]

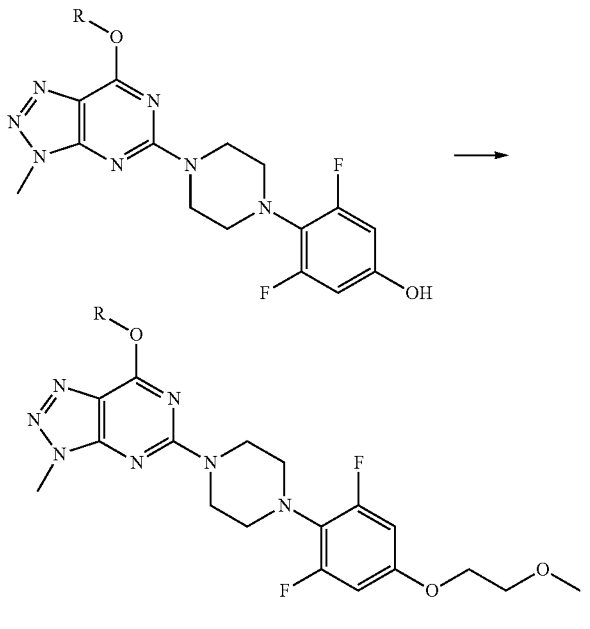

According to an embodiment of the present invention, the reaction may be performed by an alkylation reaction in which the compound represented by Chemical Formula 11 is reacted with 1-halo-2-methoxyethane (for example, 1-bromo-2-methoxyethane).

In the reaction, any organic solvent conventionally used in alkylation reactions may be used. For example, the solvent may be acetonitrile, tetrahydrofuran, 1,4-dioxane, acetone, dimethyl sulfoxide, dimethyl acetamide, dimethyl formamide, or a mixture thereof. Specifically, dimethylformamide may be used, but the solvent is not limited thereto.

Further, the reaction may be performed at 50 to 100° C., and more specifically, may be performed at 60 to 80° C., but is not limited thereto.

According to the preparation method disclosed in International Publication No. WO 2016/006974, the compound represented by Chemical Formula I is synthesized through an 11-step process. Further, the preparation method was not suitable for mass production since it utilized microwaves or multiple column purification steps. However, according to the preparation method of the present invention, neither synthesis route A nor B requires a large number of processes, with 8 or 7 steps. In addition, steps (A-1) to (A-8) of synthetic route A and steps (B-1) to (B-7) of synthetic route B are not proceeded by microwave and column purification process, and they are suitable for mass production as efficiently can produce compounds with high yield and high purity.

Furthermore, the compounds represented by Chemical Formula 1 to 11 and Chemical Formula Ia as prepared and used in Steps (A-1) through (A-8), Steps (B-1) through (B-7) above are all useful intermediates for preparing the triazolopyrimidinone derivative compounds represented by Chemical Formula I.

Advantageous Effects

The preparation method of the present invention can achieve the development of efficient processes and require fewer processes compared to the conventional preparation methods, which allows for the preparation of a triazolopyrimidinone derivative compound with high purity and high yield by crystallization without the need for column purification and microwave reaction, thereby significantly lowering the production cost, which is economical, and being suitable for mass production.

BEST MODE

Hereinafter, the following Examples are presented to enhance comprehension of the present invention. These Examples are only provided to more easily understand the present invention, and do not impose limitations on the content of the present invention.

Example 1

In Example 1 of the present invention, a triazolopyrimidinone derivative compound represented by Chemical Formula I was prepared according to the following Reaction Scheme I:

[Reaction Scheme I]

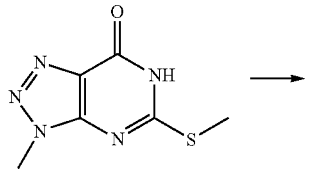

-continued

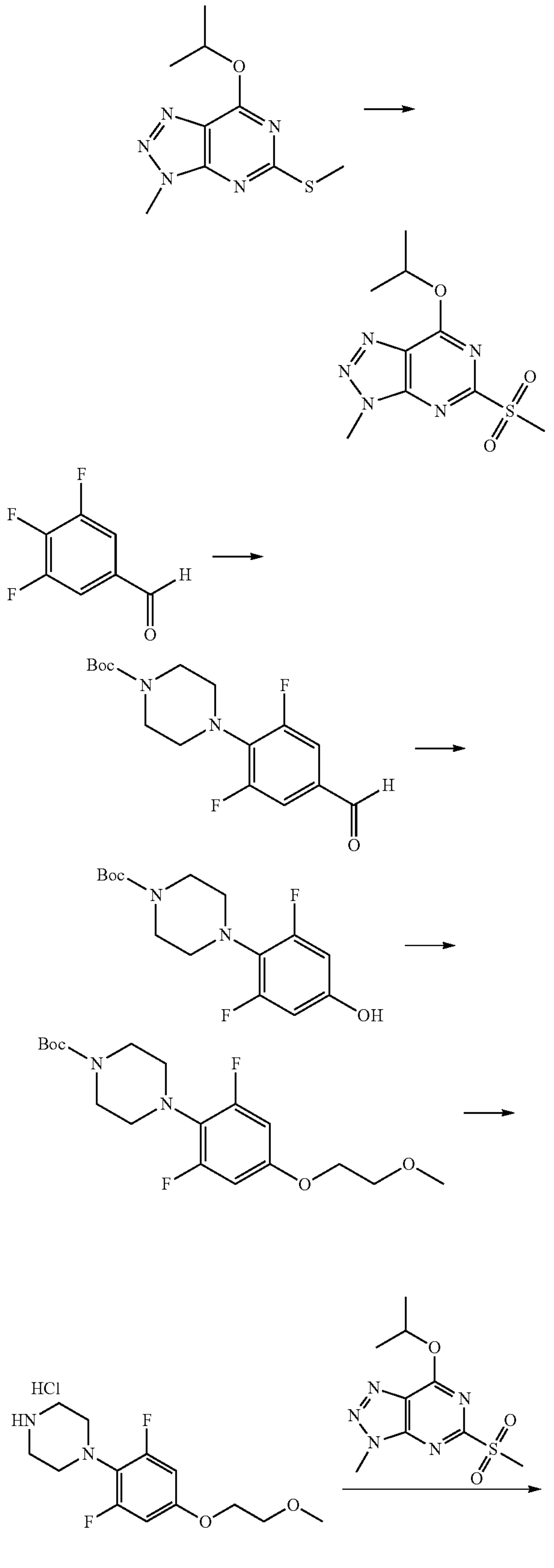

-continued

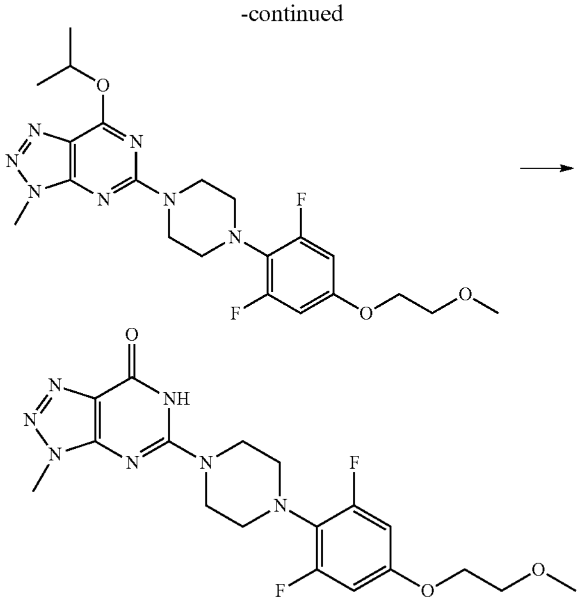

Step 1: Preparation of 7-isopropoxy-3-methyl-5-(methylthio)-3H-[1,2,3]triazolo[4,5-d]pyrimidine 3-Methyl-5-(methylthio)-3,6-dihydro-7H-[1,2,3]triazolo[4,5-d]pyrimidin-7-one (15 g, 76.1 mmol) was diluted in 76 mL of dimethylformamide. Cesium fluoride (46.2 g, 304.2 mmol) and isopropyl iodide (38.1 g, 228.2 mmol) were added thereto, the internal temperature was raised to 75 to 80° C., and the reaction mixture was stirred for 2 hours. When the reaction was completed, the mixture was cooled to room temperature, 300 mL of ethyl acetate was added, and the mixture was stirred for 10 minutes. The formed crystals were filtered through Celite filtration, and 120 mL of 5% brine was added to the filtrate and stirred for 10 minutes. The organic layer was washed twice more with 120 mL of 5% brine. The organic layer was dried over anhydrous sodium sulfate, filtered and concentrated under reduced pressure. To the concentrated residue, 50 mL of isopropanol was added, warmed to 40° C., and stirred for 30 minutes. The precipitated crystals were stirred at 5 to 10° C. for 30 minutes, filtered, and dried under reduced pressure to afford the desired product (11.3 g, 62%) as a light yellow solid.

$^1$H-NMR 400 Hz (DMSO-$d_6$): 5.62 (m, 1H), 4.15 (s, 3H), 2.61 (s, 3H), 1.44 (d, J=8 Hz, 6H).

LCMS (ESI, m/z): 240.1 [M+H$^+$].

Step 2: Preparation of 7-isopropoxy-3-methyl-5-(methylsulfonyl)-3H-[1,2,3]triazolo[4,5-d]pyrimidine The 7-isopropoxy-3-methyl-5-(methylthio)-3H-[1,2,3]triazolo[4,5-d]pyrimidine prepared in Step 1 (10 g, 41.8 mmol) was diluted in 70 mL of tetrahydrofuran, and stirred while cooling the internal temperature to 5 to 10° C. Oxone (38.5 g, 125.3 mmol) was dissolved in 200 mL of purified water and then added dropwise to the reaction solution for 30 minutes. After the dropwise addition was completed, the internal temperature was raised to 35 to 40° C. and the reaction mixture was stirred for 2 hours. When the reaction was completed, the reaction solution was concentrated under reduced pressure, 100 mL of dichloromethane was added, and the organic layer was extracted. The aqueous layer was extracted with 100 mL of dichloromethane, the organic layers were combined, dried over anhydrous sodium sulfate, filtered and concentrated under reduced pressure. To the concentrated residue, 50 mL of isopropanol was added, warmed to 75° C., and stirred for 30 minutes. The precipitated crystals were stirred at 5 to 10° C. for 30 minutes, filtered, and dried under reduced pressure to afford the desired product (9.9 g, 87%) as an off-white solid.

$^1$H-NMR 400 Hz (DMSO-$d_6$): 5.74 (m, 1H), 4.30 (s, 3H), 3.47 (s, 3H), 1.50 (d, J=6.4 Hz, 6H).

LCMS (ESI, m/z): 272.0 [M+H$^+$].

Step 3: Preparation of tert-butyl 4-(2,6-difluoro-4-formylphenyl)piperazine-1-carboxylate In dimethyl sulfoxide (25 mL), 3,4,5-trifluorobenzaldehyde (5 g, 31.2 mmol), Boc-piperazine (5.8 g, 31.2 mmol), and lithium carbonate (7.3 g, 94 mmol) were diluted, and the mixture was then stirred for 3 hours at the internal temperature of 115 to 120° C. Upon completion of the reaction, the reaction solution was cooled to room temperature, diluted in a mixture of 125 mL of cold water and 50 mL of ethyl acetate, and stirred for 10 minutes. The insoluble material was removed by Celite filtration. The organic layer of the filtrate was separated, dried over anhydrous sodium sulfate, filtered, and concentrated under reduced pressure. The next reaction was performed without purifying the residue.

Step 4: Preparation of tert-butyl 4-(2,6-difluoro-4-hydroxyphenyl)piperazine-1-carboxylate The tert-butyl 4-(2,6-difluoro-4-formylphenyl)piperazine-1-carboxylate prepared in Step 3 was dissolved in 102 mL of dichloromethane and stirred while cooling to the internal temperature of −15 to −10° C. Meta-chloroperoxybenzoic acid (8.08 g, 46.8 mmol) was added slowly in portions and stirred for 2 hours while maintaining the internal temperature at −10 to 10° C. 2N aqueous sodium hydroxide solution (78 mL, 156 mmol) was added dropwise to the reaction solution, which was gradually brought to room temperature, and stirred for 2 hours. Upon completion of the reaction, the water layer was separated and adjusted to pH 6 with 1N aqueous hydrochloric acid solution at 0 to 5° C., and 90 mL of tert-butyl methyl ether was then added and stirred for 10 minutes. The organic layer was extracted and washed with 30 mL of aqueous sodium bicarbonate solution. The organic layer was dried over anhydrous sodium sulfate, filtered and concentrated under reduced pressure. To the residue, 35 mL of isopropanol was added and the mixture was stirred at room temperature for 3 hours. The reaction mixture was filtered and dried under reduced pressure to afford the desired product (3.9 g, 40%) as a pale yellow solid.

$^1$H-NMR 400 Hz (MeOD): 6.33 (d, J=8.2 Hz, 2H), 4.63 (S, 1H), 3.52 (S, 4H), 3.00 (S, 4H), 1.49 (S, 9H).

LCMS (ESI, m/z): 315.1 [M+H$^+$].

Step 5: Preparation of tert-butyl 4-(2,6-difluoro-4-(2-methoxyethoxy)phenyl)piperazine-1-carboxylate The tert-butyl 4-(2,6-difluoro-4-hydroxyphenyl)piperazine-1-carboxylate (20 g, 63.6 mmol) prepared in Step 4 was diluted in acetonitrile. Calcium carbonate (26.4 g, 190.9 mmol) and 1-bromo-2-methoxyethane (13.3 g, 95.5 mmol) were added, and the reaction mixture was then raised to 75 to 85° C. and stirred at reflux for 8 hours. After the reaction was completed, the reaction solution was concentrated under reduced pressure. To the residue, 140 mL of purified water and 280 mL of ethyl acetate were added and stirred at room temperature for 15 minutes. The organic layer was separated, dried over anhydrous sodium sulfate, filtered, and concentrated under reduced pressure. The next reaction was performed without purifying the residue.

Step 6: Preparation of 1-(2,6-difluoro-4-(2-methoxyethoxy)phenyl)piperazine hydrochloride To the reactor, 240 mL of methanol was added and cooled to the internal temperature below 5° C., and then acetyl chloride (31.3 mL, 439 mmol) was slowly added and stirred for 15 minutes. The tert-butyl 4-(2,6-difluoro-4-(2-methoxyethoxy)phenyl)piperazine-1-carboxylate prepared in Step 5 was dissolved in 64 mL of dichloromethane and then slowly added to the reactor, and the internal temperature was raised to 40 to 45° C. and stirred for 2 hours. After the reaction was completed, the reaction solution was concentrated under reduced pressure, and 60 mL of methanol was added to the residue and dissolved by stirring at room temperature. The internal temperature was cooled to 15 to 20° C., and 180 mL of tert-butyl methyl ether was added dropwise and stirred for 30 minutes. The precipitated crystals were filtered and dried under reduced pressure to afford the desired product (14.2 g, 72%) as an off-white solid.

$^1$H-NMR 400 Hz (DMSO-$d_6$): 9.25 (brs, 2H), 6.85-6.64 (m, 2H), 4.12-4.02 (m, 2H), 3.65-3.58 (m, 2H), 3.28 (s, 3H), 3.25-3.18 (m, 4H), 3.17-3.09 (m, 4H).

LCMS (ESI, m/z): 273.0 [M+H$^+$]. (Free form)

Step 7: Preparation of 5-(4-(2,6-difluoro-4-(2-methoxyethoxy)phenyl)piperazin-1-yl)-7-isopropoxy-3-methyl-3H-[1,2,3]triazolo[4,5-d]pyrimidine The 7-isopropoxy-3-methyl-5-(methylsulfonyl)-3H-[1,2,3]triazolo[4,5-d]pyrimidine prepared in Step 2 (10 g, 36.9 mmol) was diluted in 146 mL of ethanol, then diisopropylethylamine (19.3 mL, 110.5 mmol) and 1-(2,6-difluoro-4-(2-methoxyethoxy)phenyl)piperazine hydrochloride (13.1 g, 42.4 mmol) prepared in Step 6 were added, the temperature was raised to 60 to 80° C., and the reaction mixture was refluxed and stirred for 3 hours. After the reaction was completed, the reaction solution was concentrated under reduced pressure, 150 mL of dichloromethane and 53 mL of water were added to the residue, and the layers were separated. The aqueous layer was extracted twice with 50 mL of dichloromethane. The organic layers were combined, washed with 50 mL of 1N aqueous hydrochloric acid solution and 50 mL of 5% brine, dried over anhydrous sodium sulfate, and filtered. To the filtrate, 2 g of activated carbon was added and stirred for 30 minutes. The filtrate was filtered through Celite and concentrated under reduced pressure. To the concentrated residue, 30 mL of dichloromethane was added to dissolve, then 200 mL of diisopropyl ether was added dropwise and stirred at 5 to 10° C. for 1 hour. The precipitated crystals were filtered and dried under reduced pressure to afford the desired product (15.1 g, 89%) as an off-white solid.

$^1$H-NMR 400 Hz (DMSO-$d_6$): 6.77-6.69 (m, 2H), 5.55 (m, 1H), 4.09-4.06 (m, 2H), 3.99 (s, 3H), 3.93 (t, J=4.8 Hz, 4H), 3.64-3.62 (m, 2H), 3.28 (s, 3H), 3.09 (t, J=4.8 Hz, 4H), 1.42 (d, J=6.4 Hz, 6H).

LCMS (ESI, m/z): 464.1 [M+H$^+$].

Step 8: Preparation of 5-(4-(2,6-difluoro-4-(2-methoxyethoxy)phenyl)piperazin-1-yl)-3-methyl-3,6-dihydro-7H-[1,2,3]triazolo[4,5-d]pyrimidin-7-one To the 5-(4-(2,6-difluoro-4-(2-methoxyethoxy)phenyl)piperazin-1-yl)-7-isopropoxy-3-methyl-3H-[1,2,3]triazolo[4,5-d]pyrimidine (15 g, 32.4 mmol) prepared in Step 7, 92 mL of acetic acid and 16.1 mL of sulfuric acid were added, warmed to the internal temperature of 45 to 50° C., and stirred for 3 hours. After the reaction was completed, the reaction solution was cooled to room temperature, and 230 mL of purified water was added dropwise for 30 minutes with stirring. After the dropwise addition was completed, the internal temperature was cooled to 5 to 10° C., and the mixture was stirred for 1 hour. The precipitated crystals were filtered and diluted in 150 mL of acetone, then the internal temperature was raised to 40 to 45° C., and the mixture was stirred for 1 hour. The reaction solution was cooled gradually to 5 to 10° C. and 150 mL of purified water was added. The precipitated crystals were stirred for 30 minutes, filtered, and dried under reduced pressure to afford the desired product (11.5 g, 84%) as an off-white solid.

$^1$H-NMR 400 Hz (DMSO-$d_6$): 11.29 (brs, 1H), 6.74 (d, J=11.2 Hz, 2H), 4.08 (t, J=4.4 Hz, 2H), 3.92 (s, 3H), 3.82-3.76 (m, 4H), 3.62 (t, J=4.4 Hz, 2H), 3.29 (s, 3H), 3.12-3.06 (m, 4H).

LCMS (ESI, m/z): 422.1 [M+H$^+$].

Example 2

In Example 2 of the present invention, the triazolopyrimidinone derivative compound represented by Chemical Formula I was prepared according to the following Reaction Scheme II:

[Reaction Scheme II]

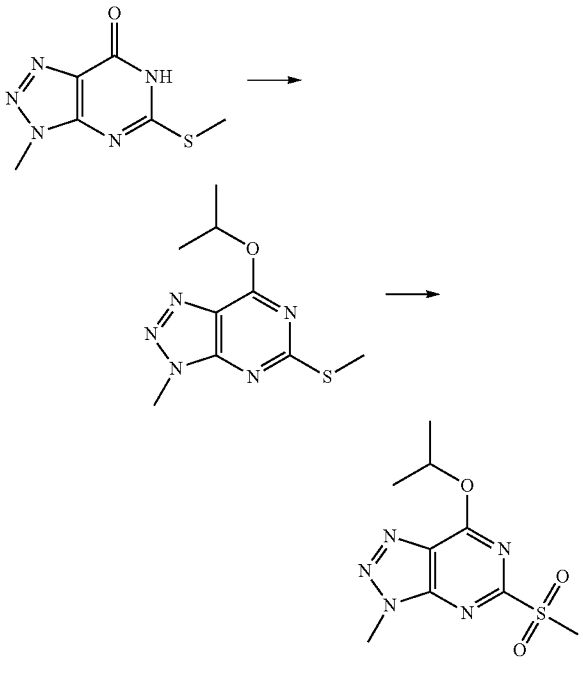

-continued

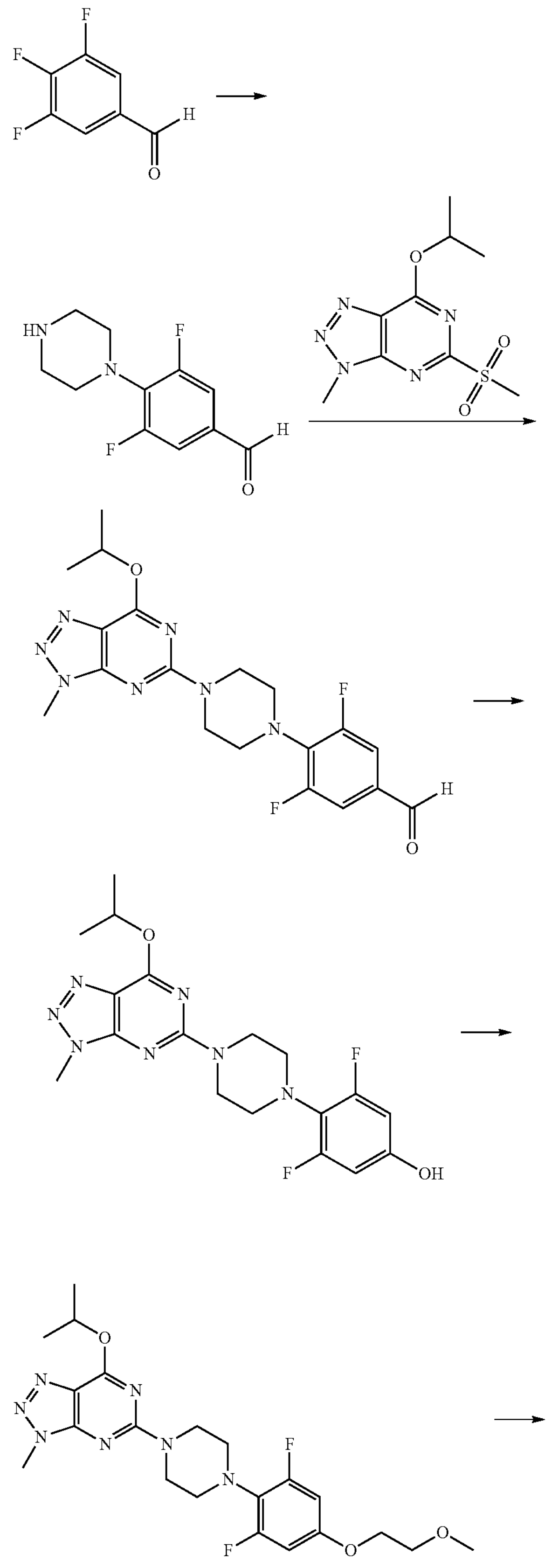

-continued

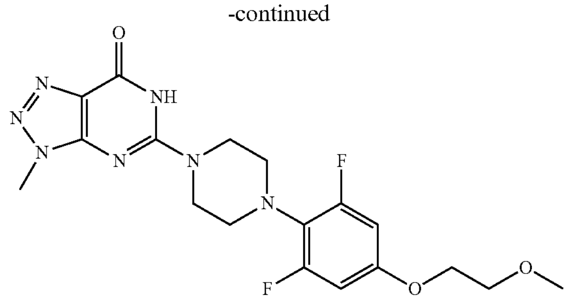

Step 1: Preparation of 3,5-difluoro-4-(piperazin-1-yl)benzaldehyde

In dimethoxyethane (50 mL), 3,4,5-trifluorobenzaldehyde (4 g, 24.99 mmol), piperazine (6.46 g, 75 mmol), and potassium carbonate (6.91 g, 50 mmol) were diluted, and the mixture was then stirred at the internal temperature of 75 to 80° C. for 20 hours. When the reaction was completed, the reaction solution was cooled to 0 to 5° C. and adjusted to pH 2 by adding a 2N aqueous hydrochloric acid solution. The aqueous layer was washed twice with 50 mL of dichloromethane and then adjusted to neutral with 1N aqueous sodium hydroxide solution. To the aqueous layer, 100 mL of dichloromethane was added, then the organic layer was extracted, dried over anhydrous sodium sulfate, filtered and concentrated under reduced pressure to afford the desired product (4.65 g, 82%) as a yellow solid.

$^{1}$H-NMR 400 Hz (DMSO-$d_6$): 9.80 (s, 1H), 7.56-7.54 (d, J=8.2 Hz, 2H), 3.19 (s, 4H), 2.79 (s, 4H).

LCMS (ESI, m/z): 227.1 [M+H$^+$].

Step 2: Preparation of 3,5-difluoro-4-(4-(7-isopropoxy-3-methyl-3H-[1,2,3]triazolo[4,5-d]pyrimidin-5-yl)piperazin-1-yl)benzaldehyde The 7-isopropoxy-3-methyl-5-(methylsulfonyl)-3H-[1,2,3]triazolo[4,5-d]pyrimidine prepared in Step 2 of Example 1 (1 g, 3.69 mmol) and 3,5-difluoro-4-(piperazin-1-yl)benzaldehyde (0.959 g, 4.24 mmol) prepared in Step 1 of Example 2 were diluted in 15 mL of dimethylacetamide, warmed to 110 to 120° C., and stirred for 2 hours. After the reaction was completed, the reaction solution was cooled to room temperature and diluted with 75 mL of ethyl acetate and 30 mL of water, and the organic layer was separated and washed with brine. The organic layer was dried over anhydrous sodium sulfate, filtered and concentrated under reduced pressure. To the concentrated residue, 5 mL of isopropanol was added and stirred for 30 minutes at room temperature. The precipitated crystals were filtered, washed with isopropanol, and dried under reduced pressure to afford the desired product (1.25 g, 81%) as a pale yellow solid.

$^{1}$H-NMR 400 Hz ($CDCl_3$): 9.81 (s, 1H), 7.44-7.36 (m, 2H), 5.65-5.55 (m, 1H), 4.07 (s, 3H), 4.05-4.03 (t, J=5.0 Hz, 4H), 3.43 (s, 4H), 1.50-1.48 (d, J=6.2 Hz, 6H).

LCMS (ESI, m/z): 418.0 [M+H$^+$].

Step 3: Preparation of 3,5-difluoro-4-(4-(7-isopropoxy-3-methyl-3H-[1,2,3]triazolo[4,5-d]pyrimidin-5-yl)piperazin-1-yl)phenol The 3,5-difluoro-4-(4-(7-isopropoxy-3-methyl-3H-[1,2,3]triazolo[4,5-d]pyrimidin-5-yl)piperazin-1-yl)benzaldehyde prepared in Step 2 (1 g, 2.4 mmol) was diluted in 8 mL of dichloromethane, then meta-chloroperoxybenzoic acid (1076 mg, 4.8 mmol) was added slowly in portions at −10 to 0° C. and stirred for 2 hours while maintaining the internal temperature at −10 to 10° C. 2N aqueous sodium hydroxide solution (9.6 mL, 19.2 mmol) was added dropwise to the reaction solution, which was gradually brought to room temperature, and stirred for 2 hours. Upon completion of the reaction, the water layer was separated and adjusted to pH 6 with 1N aqueous hydrochloric acid solution at 0 to 5° C., and 50 mL of tert-butyl methyl ether was then added and stirred for 10 minutes. The organic layer was extracted and washed with 10 mL of aqueous sodium bicarbonate solution. The organic layer was dried over anhydrous sodium sulfate, filtered and concentrated under reduced pressure. To the residue, 3 mL of isopropanol was added and the mixture was stirred at room temperature for 1 hour. The reaction mixture was filtered and dried under reduced pressure to afford the desired product (388 mg, 40%) as a pale yellow solid.

$^1$H-NMR 400 Hz (DMSO-$d_6$): 6.44-6.42 (d, J=11.0 Hz, 2H), 5.57-5.51 (m, 1H), 3.99 (s, 3H), 3.92 (s, 3H), 1.42-1.41 (d, J=6.2 Hz, 6H).

LCMS (ESI, m/z): 406.0 [M+H$^+$].

Step 4: Preparation of 5-(4-(2,6-difluoro-4-(2-methoxyethoxy)phenyl)piperazin-1-yl)-7-isopropoxy-3-methyl-3H-[1,2,3]triazolo[4,5-d]pyrimidine The 3,5-difluoro-4-(4-(7-isopropoxy-3-methyl-3H-[1,2,3]triazolo[4,5-d]pyrimidin-5-yl)piperazin-1-yl)phenol prepared in Step 3 (1 g, 2.5 mmol) was diluted in 10 mL of dimethylformamide, then potassium carbonate (1.02 g, 7.4 mmol) was added and stirred at 65 to 70° C. for 7 hours. After the reaction was completed, 200 mL of purified water and 550 mL of ethyl acetate were added and stirred at room temperature for 15 minutes. The organic layer was separated, dried over anhydrous sodium sulfate, filtered, and concentrated under reduced pressure. Dichloromethane and diisopropyl ether were added dropwise to the concentrated residue to precipitate crystals. The precipitated crystals were filtered and dried under reduced pressure to afford the desired product (780 mg, 68%) as an off-white solid.

$^1$H-NMR 400 Hz (DMSO-$d_6$): 6.77-6.69 (m, 2H), 5.55 (m, 1H), 4.09-4.06 (m, 2H), 3.99 (s, 3H), 3.93 (t, J=4.8 Hz, 4H), 3.64-3.62 (m, 2H), 3.28 (s, 3H), 3.09 (t, J=4.8 Hz, 4H), 1.42 (d, J=6.4 Hz, 6H).

LCMS (ESI, m/z): 464.1 [M+H$^+$].

Step 5: Preparation of 5-(4-(2,6-difluoro-4-(2-methoxyethoxy)phenyl)piperazin-1-yl)-3-methyl-3,6-dihydro-7H-[1,2,3]triazolo[4,5-d]pyrimidin-7-one To the 5-(4-(2,6-difluoro-4-(2-methoxyethoxy)phenyl)piperazin-1-yl)-7-isopropoxy-3-methyl-3H-[1,2,3]triazolo[4,5-d]pyrimidine (750 mg, 1.62 mmol) prepared in Step 4, 4.6 mL of acetic acid and 0.81 mL of sulfuric acid were added, warmed to an internal temperature of 45 to 50° C., and stirred for 3 hours. After the reaction was completed, the reaction solution was cooled to room temperature, and 11 mL of purified water was added dropwise for 30 minutes with stirring. After the dropwise addition was completed, the internal temperature was cooled to 5 to 10° C., and the mixture was stirred for 1 hour. The precipitated crystals were filtered and diluted in 7.5 mL of acetone, then the internal temperature was raised to 40 to 45° C., and the mixture was stirred for 1 hour. The reaction solution was cooled gradually to 5 to 10° C. and 7.5 mL of purified water was added. The precipitated crystals were stirred for 30 minutes, filtered, and dried under reduced pressure to afford the desired product (575 mg, 84%) as an off-white solid.

$^1$H-NMR 400 Hz (DMSO-$d_6$): 11.29 (brs, 1H), 6.74 (d, J=11.2 Hz, 2H), 4.08 (t, J=4.4 Hz, 2H), 3.92 (s, 3H), 3.82-3.76 (m, 4H), 3.62 (t, J=4.4 Hz, 2H), 3.29 (s, 3H), 3.12-3.06 (m, 4H).

LCMS (ESI, m/z): 422.1 [M+H$^+$].

While the foregoing has described in detail certain aspects of the present invention, it will be apparent to one of ordinary skill in the art that these specific descriptions are merely preferred embodiments and are not intended to limit the scope of the invention. Therefore, the substantive scope of the invention will be defined by the appended claims and equivalents thereof.

The invention claimed is:

1. A process for preparing a compound represented by the Chemical Formula I:

Chemical Formula I

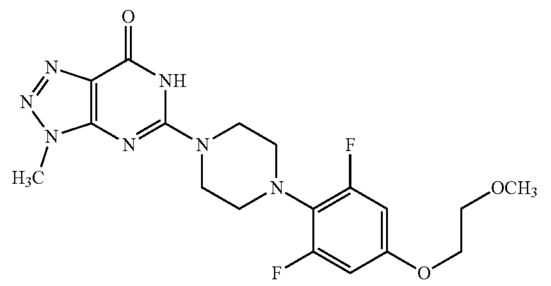

wherein the process comprises the following steps:

(A-1) reacting a compound represented by the Chemical Formula 1:

Chemical Formula 1

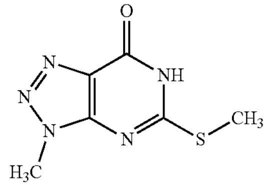

or a salt thereof, with cesium fluoride, potassium carbonate, or cesium carbonate and a compound of the following formula:

RI, wherein:

R is $C_1$-$C_6$ alkyl, $CH_2OCH_3$ (MOM), $CH_2$-phenyl, $CH_2$-(4-methoxyphenyl), C(O)$CH_3$, C(O)phenyl, Si($C_1$-$C_6$ alkyl)$_3$, or tetrahydropyranyl (THP);

to provide a protected compound represented by the Chemical Formula 2:

Chemical Formula 2

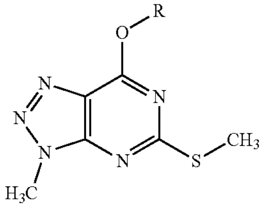

wherein:

R is $C_1$-$C_6$ alkyl, $CH_2OCH_3$ (MOM), $CH_2$-phenyl, $CH_2$-(4-methoxyphenyl), $C(O)CH_3$, C(O)phenyl, Si($C_1$-$C_6$ alkyl)$_3$, or tetrahydropyranyl (THP);

(A-2) oxidizing the protected compound represented by the Chemical Formula 2 provided in step (A-1) above with an oxidizing agent selected from the group consisting of hydrogen peroxide, benzoyl peroxide, meta-chloroperoxybenzoic acid (mCPBA), and oxone, to provide a protected compound represented by the Chemical Formula 3:

Chemical Formula 3

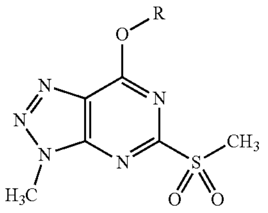

wherein:

R is $C_1$-$C_6$ alkyl, $CH_2OCH_3$ (MOM), $CH_2$-phenyl, $CH_2$-(4-methoxyphenyl), $C(O)CH_3$, C(O)phenyl, Si($C_1$-$C_6$ alkyl)$_3$, or tetrahydropyranyl (THP);

(A-3) reacting a compound represented by the Chemical Formula 4:

Chemical Formula 4

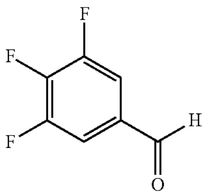

with a protected compound of the following formula:

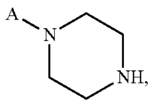

wherein:

A is $CH_2$-phenyl, $CH_2$-(4-methoxyphenyl), C(O)$OCH_2$-phenyl (Cbz), C(O)OC($CH_3$)$_3$ (Boc), C(O)$OCH_2$-fluorenyl (Fmoc), C(phenyl)$_3$, or C(4-methoxyphenyl)$_2$(phenyl) (DMT);

in the presence of a base selected from the group consisting of sodium bicarbonate, lithium carbonate, sodium carbonate, potassium carbonate, and cesium carbonate, to provide a protected compound represented by the Chemical Formula 5:

Chemical Formula 5

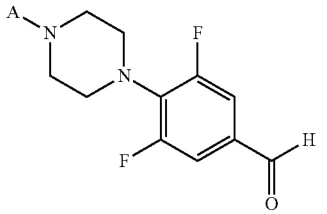

wherein:

A is $CH_2$-phenyl, $CH_2$-(4-methoxyphenyl), C(O)$OCH_2$-phenyl (Cbz), C(O)OC($CH_3$)$_3$ (Boc), C(O)$OCH_2$-fluorenyl (Fmoc), C(phenyl)$_3$, or C(4-methoxyphenyl)$_2$(phenyl) (DMT);

(A-4) oxidizing the protected compound represented by the Chemical Formula 5 provided in step (A-3) above with an oxidizing agent selected from the group consisting of ammonium persulfate, hydrogen peroxide, and meta-chloroperoxybenzoic acid (mCPBA), or a mixture thereof, in the presence of a base selected from the group consisting of sodium bicarbonate, sodium carbonate, calcium carbonate, lithium hydroxide, sodium hydroxide, and potassium hydroxide, to provide a protected compound represented by the Chemical Formula 6:

Chemical Formula 6

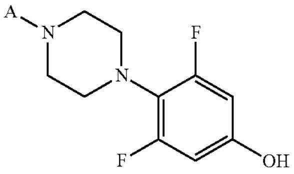

wherein:

A is $CH_2$-phenyl, $CH_2$-(4-methoxyphenyl), C(O)$OCH_2$-phenyl (Cbz), C(O)OC($CH_3$)$_3$ (Boc), C(O)$OCH_2$-fluorenyl (Fmoc), C(phenyl)$_3$, or C(4-methoxyphenyl)$_2$(phenyl) (DMT);

(A-5) alkylating the protected compound represented by the Chemical Formula 6 provided in step (A-4) above with a 1-halo-2-methoxyethane, to provide a protected compound represented by the Chemical Formula 7:

Chemical Formula 7

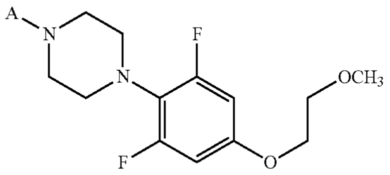

wherein:

A is $CH_2$-phenyl, $CH_2$-(4-methoxyphenyl), C(O)$OCH_2$-phenyl (Cbz), C(O)OC($CH_3$)$_3$ (Boc), C(O)$OCH_2$-fluorenyl (Fmoc), C(phenyl)$_3$, or C(4-methoxyphenyl)$_2$(phenyl) (DMT);

(A-6) reacting the protected compound represented by the Chemical Formula 7 provided in step (A-5) above with acetyl chloride in methanol, ethanol, or isopropanol, to provide a compound represented by the Chemical Formula 8:

Chemical Formula 8

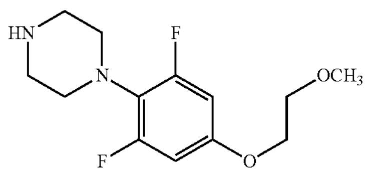

or a salt thereof;

(A-7) reacting the protected compound represented by the Chemical Formula 3 provided in step (A-2) above:

Chemical Formula 3

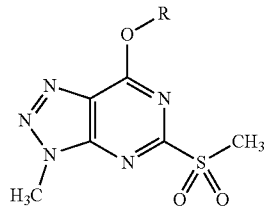

wherein:

R is $C_1$-$C_6$ alkyl, $CH_2OCH_3$ (MOM), $CH_2$-phenyl, $CH_2$-(4-methoxyphenyl), $C(O)CH_3$, C(O)phenyl, $Si(C_1$-$C_6$ alkyl$)_3$, or tetrahydropyranyl (THP);

with the compound represented by the Chemical Formula 8, provided in step (A-6) above, or a salt thereof:

Chemical Formula 8

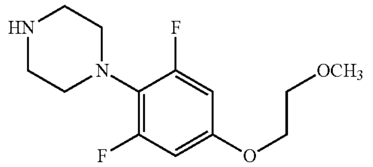

in the presence of a base selected from the group consisting of lithium carbonate, sodium carbonate, cesium carbonate, triethylamine, diisopropylethylamine, and 1,8-diazabicyclo[5.4.0]undec-7-ene (DBU), to provide a protected compound represented by the Chemical Formula Ia:

Chemical Formula Ia

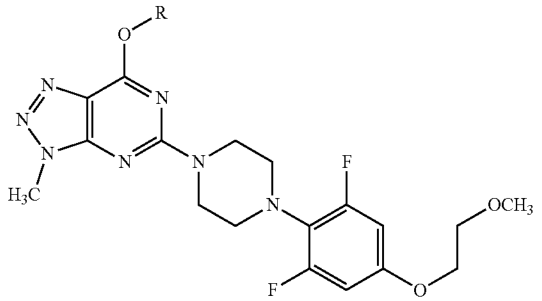

wherein:

R is $C_1$-$C_6$ alkyl, $CH_2OCH_3$ (MOM), $CH_2$-phenyl, $CH_2$-(4-methoxyphenyl), $C(O)CH_3$, C(O)phenyl, $Si(C_1$-$C_6$ alkyl$)_3$, or tetrahydropyranyl (THP); and (A-8) reacting the protected compound represented by the Chemical Formula Ia provided in step (A-7) above with an acid selected from the group consisting of acetic acid, hydrochloric acid, nitric acid, phosphoric acid, and sulfuric acid, or a mixture thereof, to provide a compound represented by the Chemical Formula I:

Chemical Formula 1

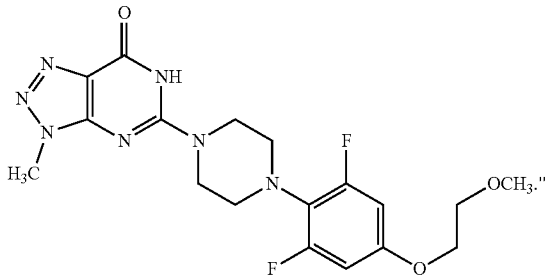

2. The process of claim 1, wherein R is $CH(CH_3)_2$.

3. The process of claim 1, wherein A is $C(O)OCH_2$-phenyl (Cbz), $C(O)OC(CH_3)_3$ (Boc), or $C(O)OCH_2$-fluorenyl (Fmoc).

4. The process of claim 3, wherein A is $C(O)OC(CH_3)_3$ (Boc).

5. The process of claim 1, wherein in Step (A-2), the oxidizing agent is meta-chloroperoxybenzoic acid (mCPBA) or oxone.

6. The process of claim 5, wherein the oxidizing agent is oxone.

7. The process of claim 1, wherein in Step (A-4), the oxidizing agent is hydrogen peroxide or meta-chloroperoxybenzoic acid (mCPBA).

8. The process of claim 7, wherein the oxidizing agent is meta-chloroperoxybenzoic acid (mCPBA).

9. A process for preparing a compound represented by the Chemical Formula I:

Chemical Formula I

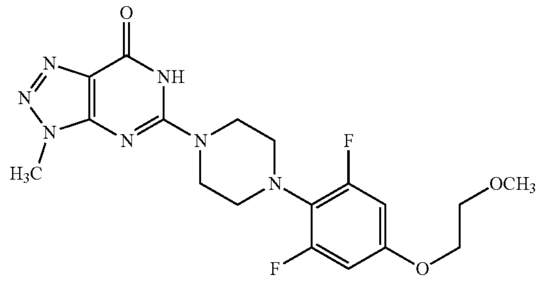

wherein the process comprises the following steps:

(B-1) reacting a compound represented by the Chemical Formula 1:

Chemical Formula 1

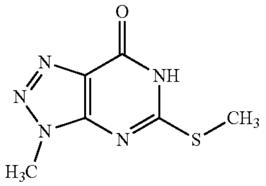

or a salt thereof, with cesium fluoride, potassium carbonate, or cesium carbonate and a compound of the following formula:

RI, wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

to provide a protected compound represented by the Chemical Formula 2:

Chemical Formula 2

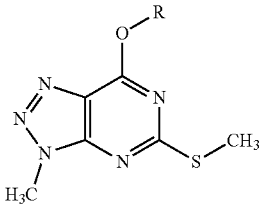

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

(B-2) oxidizing the protected compound represented by the Chemical Formula 2 provided in step (B-1) above with an oxidizing agent selected from the group consisting of hydrogen peroxide, benzoyl peroxide, meta-chloroperoxybenzoic acid (mCPBA), and oxone, to provide a protected compound represented by the Chemical Formula 3:

Chemical Formula 3

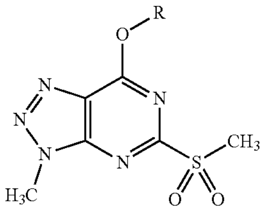

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

(B-3) reacting a compound represented by the Chemical Formula 4:

Chemical Formula 4

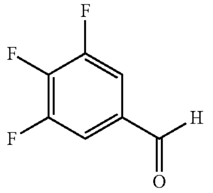

with a compound of the following formula:

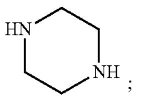

in the presence of a base selected from the group consisting of sodium bicarbonate, lithium carbonate, sodium carbonate, potassium carbonate, and cesium carbonate, to provide a compound represented by the Chemical Formula 9:

Chemical Formula 9

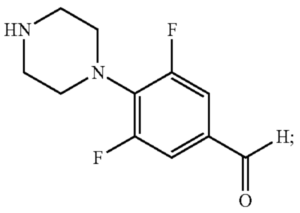

(B-4) reacting the compound represented by the Chemical Formula 9 provided in step (B-3) above with a protected compound represented by the Chemical Formula 3:

Chemical Formula 3

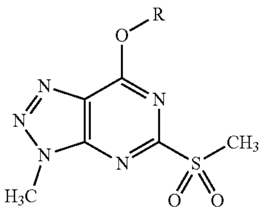

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

in the presence of a base selected from the group consisting of sodium bicarbonate, lithium carbonate, sodium carbonate, potassium carbonate, cesium carbonate, triethylamine, diisopropylethylamine, and 1,8-diazabicyclo[5.4.0]undec-7-ene (DBU), to provide a protected compound represented by the Chemical Formula 10:

Chemical Formula 10

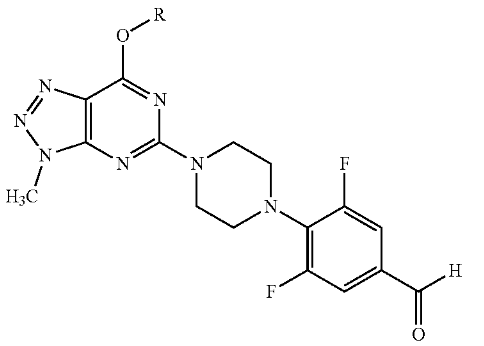

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

(B-5) oxidizing the protected compound represented by the Chemical Formula 10 provided in step (B-4) above with an oxidizing agent selected from the group consisting of ammonium persulfate, hydrogen peroxide, and meta-chloroperoxybenzoic acid (mCPBA), or a mixture thereof, in the presence of a base selected from the group consisting of sodium bicarbonate, sodium carbonate, calcium carbonate, lithium hydroxide, sodium hydroxide, and potassium hydroxide, to provide a protected compound represented by the Chemical Formula 11:

Chemical Formula 11

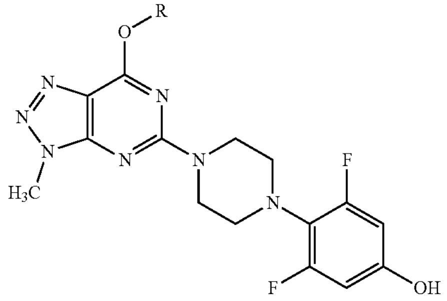

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP);

(B-6) alkylating the protected compound represented by the Chemical Formula 11 provided in step (B-5) above with a 1-halo-2-methoxyethane, to provide a protected compound represented by the Chemical Formula Ia:

Chemical Formula Ia

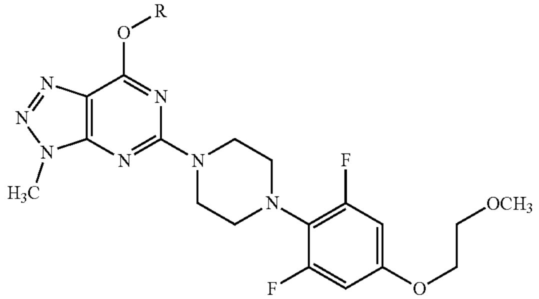

wherein:

R is $C_1$-$C_6$ alkyl, $CH_2OCH_3$ (MOM), $CH_2$-phenyl, $CH_2$-(4-methoxyphenyl), C(O) $CH_3$, C(O)phenyl, Si($C_1$-$C_6$ alkyl)$_3$, or tetrahydropyranyl (THP); and (B-7) reacting the protected compound represented by the Chemical Formula Ia provided in step (B-6) above with an acid selected from the group consisting of acetic acid, hydrochloric acid, nitric acid, phosphoric acid, and sulfuric acid, or a mixture thereof, to provide a compound represented by the Chemical Formula I:

Chemical Formula 1

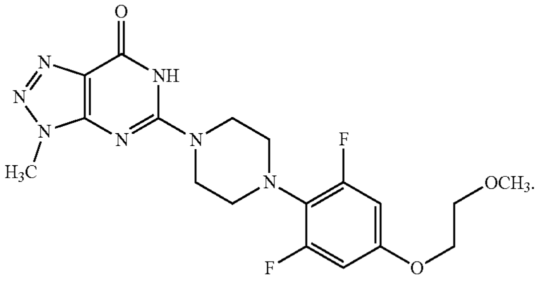

10. The process of claim 9, wherein R is $CH(CH_3)_2$.

* * * * *